United States Patent [19]

Smith, III

[11] Patent Number: 5,494,800
[45] Date of Patent: *Feb. 27, 1996

[54] ANALYTE DETECTION IN PARTICULATE-CONTAINING SAMPLES

[75] Inventor: Nathan L. Smith, III, North Andover, Mass.

[73] Assignee: CytoSignet, Inc., North Andover, Mass.

[*] Notice: The term of this patent shall not extend beyond the expiration date of Pat. No. 4,900,685.

[21] Appl. No.: 235,189

[22] Filed: Apr. 29, 1994

Related U.S. Application Data

[63] Continuation of Ser. No. 478,215, Feb. 9, 1990, abandoned, which is a continuation-in-part of Ser. No. 8,571, Jan. 29, 1987, Pat. No. 4,900,685.

[51] Int. Cl.$^6$ .................. G01N 33/555; G01N 33/569; G01N 33/539; C07K 14/195
[52] U.S. Cl. .................. 435/7.32; 435/962; 435/7.25; 436/520; 436/539; 530/395; 530/396; 530/825
[58] Field of Search ............... 435/7.32, 7.25, 435/7.3; 436/519, 523, 520, 539, 827; 530/395, 396, 825

[56] References Cited

U.S. PATENT DOCUMENTS

| | | | |
|---|---|---|---|
| 3,562,384 | 2/1971 | Arquilla et al. | 436/510 |
| 3,882,225 | 5/1975 | Patel et al. | 436/519 |
| 4,289,747 | 9/1981 | Chu | 435/7.8 |
| 4,371,515 | 2/1983 | Chu et al. | 436/544 |
| 4,398,894 | 8/1983 | Yamamoto | 436/517 |
| 4,403,037 | 9/1983 | Coates | 436/521 |
| 4,433,059 | 2/1984 | Chang et al. | 436/512 |
| 4,436,827 | 3/1984 | Tamagawa | 436/534 |
| 4,493,793 | 1/1985 | Chu | 530/303 |
| 4,526,871 | 7/1985 | Avrameas et al. | 436/504 |
| 4,529,712 | 7/1985 | Jou et al. | 436/519 |
| 4,547,466 | 10/1985 | Turanchik et al. | 436/509 |
| 4,554,257 | 11/1985 | Aladjem et al. | 436/519 |
| 4,565,789 | 1/1986 | Liotta et al. | 436/504 |
| 4,578,360 | 3/1986 | Smith | 436/518 |
| 4,587,222 | 5/1986 | Guffroy | 436/509 |
| 4,594,327 | 6/1986 | Zuk | 436/514 |
| 4,598,051 | 7/1986 | Papahadjopoulos et al. | 436/512 |
| 4,760,142 | 7/1988 | Primes et al. | 544/287 |
| 4,829,011 | 5/1989 | Gibbons | 436/512 |
| 4,894,347 | 1/1990 | Hillyard et al. | 436/540 |
| 4,900,685 | 2/1990 | Smith, III et al. | 436/519 |

FOREIGN PATENT DOCUMENTS

| | | |
|---|---|---|
| 0000102 | 12/1978 | European Pat. Off. . |
| 0034050 | 5/1981 | European Pat. Off. . |
| 0143574 | 1/1984 | European Pat. Off. . |
| 0308242 | 9/1988 | European Pat. Off. . |

OTHER PUBLICATIONS

Package Insert, Equine Immunoglobulin G Test, Hamilton–Thorn Research.
Package Insert, One–Step Whole Blood IgG Screen, Hamilton–Thorn Research.
Mandaro, R. M. et al., Bio/Technology, 5: 928–932 (1987).
Nichols et al., "Agglutination and Agglutination Inhibition Assays", In: *Laboratory Manual of Clinical Immunology*, Rose et al., Ed., (Am. Soc. Microbiol.: Washington, D.C.) pp. 49–56 (1985).
Kabat, *Structural Concepts in Immunology and Immunochemistry*, pp. 46–48 (1968).
B. E. Kemp et al., Science, 241: 1352–1354 (1988).
Guesdon, J.-L. and S. Avrameas, *J. Immunol. Meth.*, 39: 1–13 (1980).

*Primary Examiner*—Toni R. Scheiner
*Assistant Examiner*—Nancy J. Parsons
*Attorney, Agent, or Firm*—Hamilton, Brook, Smith & Reynolds

[57] ABSTRACT

A method of determining the presence and quantity of an analyte of interest in a particulate-containing sample is disclosed, as is a construct for use in the method. The method is particularly useful for determining an analyte in whole blood and in fermentation suspensions. The construct is comprised of a first moiety, which is a particulate-binding moiety and a second moiety, which binds the analyte of interest.

40 Claims, 1 Drawing Sheet

ANALYTE DETECTION IN PARTICULATE-CONTAINING SAMPLES

RELATED APPLICATION

This application is a continuation of co-pending application Ser. No. 07/478,215 filed Feb. 9, 1990, now abandoned, which is a continuation-in-part of Ser. No. 07/008,571, filed Jan. 29, 1987 (now U.S. Pat. No. 4,900,685, issued Feb. 13, 1990), the entire teachings of which are both incorporated herein by reference.

DESCRIPTION

BACKGROUND OF THE INVENTION

Immunoassays are a type of ligand-binding assay and are widely used to determine the presence and quantities of analytes (i.e., substances or chemical constituents of a sample which are being detected). Agglutination immunoassays are a type of immunoassay in which the immunochemical reaction results in clumping of particulates such as red blood cells or polymeric latex particles. The use of immunochemical reactions as a means of causing agglutination has found application in the determination of many analytes, as described in: Nichols, W. S. and R. M. Nakamura, "Agglutination and Agglutination Inhibition Assays", *Laboratory Manual of Clinical Immunology* (Rose et al., ed.) 49–56 (1985).

For example, blood typing is performed by agglutination assays in which reagent antibody is added; red blood cells in the sample clump as a result of interaction between the added reagent antibody and antigens on the cell surfaces. Hemagglutination tests are immunoassays which use specially treated red blood cells. Such tests have been used for detecting antibodies and antigens, such as rubella antibody, rheumatoid factor, hepatitis antibody, hepatitis antigen and pregnancy hormone.

Reagents used in hemagglutination assays can be red blood cells (erythrocytes) which have antigens or antibodies bound to their surfaces. Red blood cells can be stabilized by cross linking or by treatment with tanning agents. See, for example, processes such as those taught in U.S. Pat. No. 4,403,037 and U.S. Pat. No. 4,587,222. For example, U.S. Pat. No. 4,403,037 describes preparation of antigen-coated erythrocytes with a cross-linking agent for the dual purpose of stabilizing the coated erythrocytes and reducing their hemagglutinating activity. Reduction of hemagglutinating activity is described as preventing the antigen-coated erythrocytes from undergoing spontaneous agglutination in the absence of antibody specific to red-blood-cell-bound hemagglutinating antigen. U.S. Pat. No. 4,587,222 describes a reagent containing red blood cells and soluble antibodies, as well as a process for making the reagents which involves subjecting its components to treatment with aldehydes or tanning agents.

Processes such as these can increase the useful life of the reagent red cells, but such chemical treatment also converts the flexible cell membrane to a rigid membrane and alters the surface properties of the cells. In some cases these changes adversely affect the specificity of the reagent in the assay.

For these reasons, polymeric latex particles have been used instead of red blood cells in some agglutination assays, such as in the agglutination assay for rheumatoid factor described in U.S. Pat. No. 4,547,466, which describes a method of preparing latex particles having immune complexes attached to their surfaces, and use of such particles.

However, reagent red blood cells and reagent polymeric particles both have the disadvantage of being likely to agglutinate even in the absence of the analyte being determined. In the case of reagent red blood cells, nonspecific agglutination is common and results from the presence of blood group antibodies and heterophile antibodies in the sample. In the case of polymeric particles, nonspecific agglutination results from nonspecific adsorption of proteins and other molecules in the sample to the particles.

Before presently-available methods based on agglutination can be carried out, it is generally necessary to remove the red blood cells from the sample. One exception to this is seen in blood-typing analyses, for which this is not necessary. Removal of red blood cells is not only an extra step in the procedure, but also one which may remove or alter the reactivity of the analyte being determined. U.S. Pat. No. No. 4,594,327 describes an immunochromatographic method for determination of an analyte in whole blood, in which two functions are combined in one step: separation of interfering cells (e.g., red blood cells) through binding to a binding agent and determination of the analyte.

U.S. Pat. No. 4,578,360 and U.S. Pat. No. 4,529,712 describe materials designed for use in immunoassay of antigens or antibodies; methods in which they are used are not agglutination immunoassays, but rely on other techniques of detecting analyte. In U.S. Pat. No. 4,578,360, Smith describes a mixed binding reagent (MBR) containing an antigen-binding site and a label-binding site; the reagent is described as normally consisting of two antibodies. In the method described, presence of an analyte (e.g., an antigen) is determined by mixing an analyte-containing sample with the MBR and a labelled substance and determining the quantity of labelled substance bound to the label-binding site of the MBR. In U.S. Pat. No. 4,529,712, heterobifunctional reagents are described for use in conjugating substances (e.g., antigens, antibodies) to membranes of cells or liposomes, which can then be used in hemolytic or immunocytoadherence assays.

Results of agglutination assays have generally been assessed visually, as described by Nichols and Nakamura. Nonvisual methods can also be used in some cases to detect agglutination. For example, U.S. Pat. Nos. 4,398,894; 4,436, 827; and 4,554,257 describe nonvisual methods. These methods can be used for measuring hemagglutination assays.

DISCLOSURE OF THE INVENTION

The present invention relates to a method and constructs useful for ligand binding assays. In particular, it relates to a method of detecting (identifying and/or quantitating) an analyte (a substance of interest) in a particulate-containing sample by means of a ligand-binding assay which makes use of particulates, present in a sample as it is obtained, as indicator particles. It further relates to constructs and reagents useful in the present method. The method of the present invention makes it possible to perform such ligand-binding assays on particulate-containing samples, such as whole blood, without the need for pretreatment of the sample to remove or dilute particulates. In samples which are suspensions of a single type of particulate, such as samples obtained from microbial fermentation or tissue culture, the single type of particulate present serves as indicator particles in the assay performed. In samples which are suspensions of two or more types of particulates (e.g., in whole blood), one type of particulate (e.g., in whole blood, red blood cells) is selected to serve as the indicator particle.

In particular, the present invention relates to a method of detecting a substance produced by an organism, such as a bacterium, a virus, a protozoan, a parasitic worm, or Rickettsia, which is characteristic of the organism and responsible for or correlated with adverse effects (e.g., illness) in an animal or human host in which it is present. The substance is, for example, a cellular constituent (e.g., of a cell wall of a gram-negative bacterium) or a product secreted by the organism. In one embodiment, the present method is useful for detecting endotoxin in whole blood from an animal (e.g., a horse, pig, cow, other farm animal, dog cat) or a human. In this embodiment, whole blood to be analyzed is combined with a construct which includes two moieties: one which binds specifically to red blood cells, such as a lectin or an antibody, and one which binds to endotoxin. In one embodiment, the red blood cell-binding moiety is PHA-aldehyde and the endotoxin-binding moiety is the antibiotic, polymyxin B. In the present method, when a whole blood sample which contains endotoxin is combined with such a construct, agglutination of red blood cells (erythroagglutination) is inhibited (i.e., the time necessary for agglutination is greater than that necessary for agglutination of an endotoxin-free control). When endotoxin is not present in the whole blood sample, agglutination occurs. The present method is useful to detect the occurrence (presence/absence) of endotoxin in a whole blood sample, as well as to quantitate the amount of endotoxin present. In both cases, the length of time necessary for agglutination of a sample to occur, after combination with a construct of the present invention, is compared with that necessary for agglutination of an appropriate control. The quantity of endotoxin present in a sample can be determined, if desired, by comparing the time necessary for agglutination of the sample with a predetermined relationship (standard curving) between endotoxin concentration and agglutination time.

The method described has several advantages over presently-available methods. First, reagents used in the method have greater stability than those used in conventional methods. This increase in useful life occurs because, unlike reagents used in presently-available agglutination immunoassay techniques, those used in the present method contain no cells or other particulates. Second, nonspecific agglutination occurs less often than in presently-available methods because the indicator particles (which occur naturally in a nonagglutinated state) are in equilibrium with the sample and are not subject to nonspecific antibody- or adsorption-mediated agglutination. Third, because there is no chemical treatment (e.g., crosslinking, treatment with tanning agents) of the indicator particles (e.g., red blood cells or RBC), their membranes retain their flexibility, enhancing the surface contact between the particles. Thus, cell surface properties are not altered. Fourth, because the method of the present invention makes it possible to carry out ligand-binding assays on particulate-containing samples (e.g., whole blood), analytes removed by clotting or cell removing processes which are carried out prior to analysis using conventional methods, are not removed in the method of the present invention and therefore can be determined. Fifth, the method of the present invention requires no pretreatment of the sample, as is necessary before a sample is analyzed using presently-available methods. Pretreatment may result in a change in the composition of the sample and, concomitantly, a change in reactivity.

The method of the present invention is quick, simpler than presently available procedures and of value in human health care (e.g., in tests on blood samples), animal health care (e.g., in tests on blood and semen samples), the food processing industry and the pharmaceutical industry. It is particularly valuable in these contexts because it can be used in assays of whole blood and other samples (e.g., fermentation suspensions) which contain particulates, without first having to remove the particulates.

BRIEF DESCRIPTION OF THE DRAWING

As shown in FIG. 1, target site 1 can be a portion or region of a substance 2 which has additional components.

Specific binding site 5 is complementary to target site 1 and is a molecule or a portion of a molecule which can specifically interact with its complementary target site resulting in the formation of a ligating bond. As also shown in FIG. 1, specific binding site 5 can be a portion or region of a substance 6 which has additional components.

Figure 1:
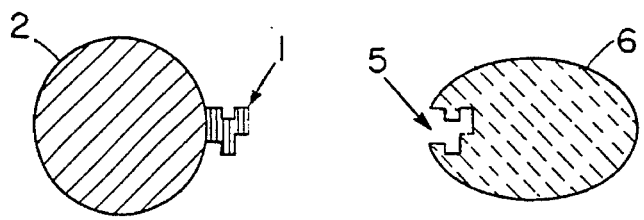
FIG. 1 is a schematic representation of a specific binding pair. One member of the pair has a target site 1 and the other has a specific binding site 5; target site 1 and specific binding site 5 in such a pair are complementary to each other. Target site 1 is a molecule or portion of a molecule which has a chemical configuration which can form a ligating bond with complementary binding site 5.
Figure 2:
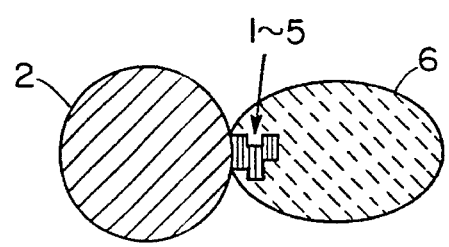

FIG. 2 shows ligating bond 1–5 formed between the two components of the specific binding pair of FIG. 1. Ligating bond 1–5 is formed between target site 1 and its complementary specific binding site 5.

Figure 3:
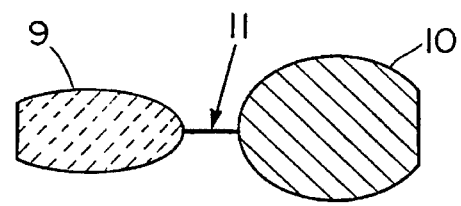

FIG. 3 is a schematic representation of the construct of the present invention, which is comprised of two moieties: 1) a moiety 9 which has either a specific binding site or a target site which forms a ligating bond with an appropriate site on particulates (indicator particles) present in a sample to be analyzed and 2) a moiety 10 which has either a specific binding site or a target site which forms a ligating bond with an appropriate site on an analyte of interest present in the sample. Moiety 9 and moiety 10 are joined into the construct of the present invention through link 11.

Figure 4A:
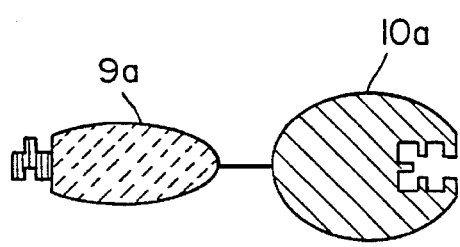

FIGS. 4a–4d depict four configurations of the construct of the invention. FIG. 4a shows a construct of the present invention in which moiety 9a has a target site and moiety 10a has a non-complementary specific binding site.

Figure 4B:
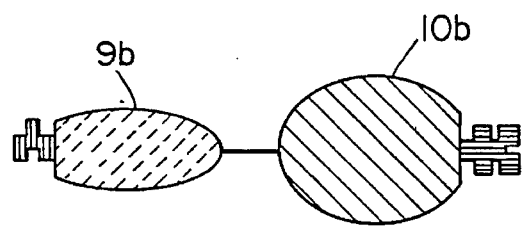

FIG. 4b shows a construct of the present invention in which each moiety has a target site; the target site of moiety 9b is different from the target site of moiety 10b.

Figure 4C:
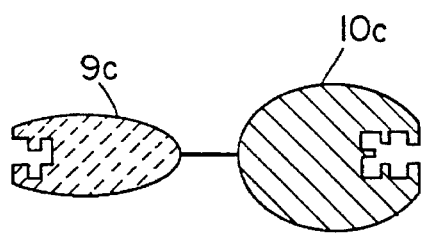

FIG. 4c shows a construct of the present invention in which each moiety has a specific binding site; the binding site of moiety 9c is different from the binding site of moiety 10c.

Figure 4D:
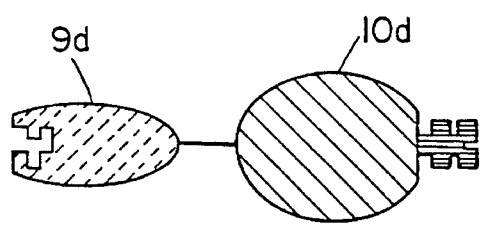

FIG. 4d shows a construct of the present invention in which moiety 9d has a specific binding site and moiety 10d has a non-complementary target site.

DETAILED DESCRIPTION OF THE INVENTION

The present invention relates to a method of carrying out ligand-binding assays, particularly immunoassays, and compositions (i.e., constructs and reagents) useful in such assays. It makes use of the fact that particulates present in a sample, as it is obtained from an individual or animal, can be used as indicator particles in an assay to determine the presence and quantity of a bindable substance (analyte) in the sample. The method of the present invention can be carried out on particulate-containing samples, without pretreatment of the sample or processing to remove the particulates.

In particular, the present invention relates to a method of carrying out ligand-binding assays of whole blood or semen obtained from humans and from animals, such as horses, cattle, pigs, other farm animals and pets, such as dogs and cats. The method of the present invention has been shown to be useful in detecting endotoxin in blood samples from horses and in monitoring the course of endotoxin levels in response to treatment. It is also useful for quantitating endotoxin levels in a whole blood sample. As described in greater detail below, the present method of detecting endotoxin is based on a determination of the extent to which inhibition of erythrocyte agglutination (erythroagglutination) occurs when an appropriate construct is combined with a sample to be analyzed. It has been demonstrated that when the present method is carried out, there is a reliable correlation between the endotoxin concentration of a sample and the extent to which sample agglutination (i.e., erythrocyte agglutination) occurs. That is, in the absence of endotoxin, agglutination of erythrocytes present in a whole blood sample occurs when the sample is combined with a construct of the present invention. In the presence of endotoxin, however, erythrocyte agglutination is inhibited (i.e., reduced or prevented). This is evidenced by the time necessary, after combination of a whole blood sample with a selected construct, for erythrocyte agglutination to occur, as compared with the time necessary for agglutination of a control which does not contain endotoxin.

The construct of the present invention useful in endotoxin detection includes two moieties which have been covalently bonded to each other: one moiety which binds red blood cells present in the blood sample being analyzed and one moiety which specifically binds endotoxin. For example, as described in Example II, a construct which is PHA-aldehyde and polymyxin B, covalently bound to one another, has been used in the present method to detect endotoxin in horses diagnosed as having a variety of conditions associated with elevated endotoxin levels. Preparation of the construct is also described in Example II. Alternatively, either or both components can be an antibody which specifically binds, respectively, red blood cells or endotoxin.

For purposes of defining and describing this invention, the following definitions are provided:

(1) Analyte (symbolized herein as "A"): a substance being detected in a particulate-containing sample.

(2) Binding site: that portion of a molecule, or multi-molecule combination, which specifically interacts with a complementary chemical or physical configuration, referred to as a target site, such that, under appropriate conditions, the interaction results in formation of a ligating bond between the binding site and the target site. The bond is symbolized herein as "~". A binding site 5 is shown in FIG. 1.

(3) get site: that portion of a molecule or multi-molecule combination which has the chemical or physical properties or characteristics necessary for forming a ligating bond "~" with a binding site. A target site 1 is depicted in FIG. 1.

(4) Indicator particles: (symbolized herein as "P"): Any of a wide variety of particulates which are capable of being suspended in an aqueous environment. They are generally between 0.01 and 50 microns in diameter and comprise a heterogeneous mixture of chemical compounds encapsulated by a boundary membrane or film. Included in this definition are cells found in nature and subcellular structures such as nuclei, mitchondria, etc. Indicator particles have one or more binding site(s) and/or target site(s) available to form one or more ligating bond(s) with their target site(s) or binding site(s), respectively.

(5) Construct (symbolized herein as "p-a" and "a-p", which are equivalent and shown in FIGS. 3 and 4): A chemical compound designed and synthesized in such a manner as to chemically bind or otherwise join two moieties into one molecule: one moiety which binds to indicator particles and a second moiety which binds to an analyte of interest. In the construct represented in FIG. 3, moiety 9 binds to an indicator particle and moiety 10 binds to an analyte of interest. Each moiety has either a binding site or a target site and has specificity distinct from (i.e., different from) and not complementary to the other moiety present in the construct. Examples of constructs of the present invention are represented in FIG. 4.

Using the method and compositions of the present invention, it is possible to detect the presence of an analyte in a particulate-containing sample by incorporating into the sample a construct capable of binding or joining the analyte and the indicator particles. Particulates in the sample as it is obtained (i.e., particulates do not need to be added to the sample to be analyzed) are used as indicator particles and are referred to in that manner. In a particulate-containing sample in which only one type of particulate occurs, the particulate serves as an indicator particle. However, in particulate-containing samples in which more than one type of particulate occurs, a specific type or specific types of particulate(s) is/are selected to serve as the indicator particle(s). For example, in whole blood, in which several types of particulates are present, red blood cells can be used as the indicator particle.

The construct used in the method of the present invention is designed and synthesized in such a way that two moieties are chemically bound or otherwise joined into one molecule, as shown in FIG. 3. One of the moieties in the construct binds to particulates in the sample; the other binds to the analyte of interest. Each of the moieties has a target site or a binding site and has specificity distinct from (i.e., different from) and not complementary to that of the other moiety. In those embodiments of the present method in which the presence of the analyte of interest is indicated by inhibition of agglutination of the sample, the construct used has two or more binding sites which bind to indicator particles present in the sample and at least one binding site which binds to the analyte of interest.

In one embodiment of the present invention, referred to as the direct method of analysis, the construct is combined with a particulate-containing sample to be analyzed. This method is appropriate for detecting analytes which can bind at least two construct molecules. If the analyte of interest is present in the sample, the result is agglutination or clumping of the indicator particles into a network comprised of the analyte, construct and indicator particles. As shown in FIG. 2, a ligating bond is formed as a result of the reaction between a specific binding site and a complementary target site. For example, chemical bonds, such as covalent bonds, hydrogen bonds, ionic bonds or salt bridges, hydrophobic interactions, etc., are formed between the specific binding site and the target site. FIG. 2 represents a ligating bond between 1 and 5, as a result of which 2 and 6 are joined. The presence and concentration of the analyte are determined by detecting the occurrence of agglutination of the particles and measuring the extent to which it occurs. The particulates thus serve as indicator particles.

In a second embodiment of the present invention, referred to as the indirect method of analysis, the construct as described above is used in combination with a second compound, referred to as a reagent. In this embodiment, the construct (which binds analyte or contains analyte and binds indicator particles), and the reagent, which is a polymeric form of the analyte entity or a polymeric form of the specific binding partner for the analyte, are combined with a sample to be analyzed. In the first case, in which a poly-analyte reagent is used, reagent can bind two or more construct molecules. In the second, in which poly-specific binding partner or agent is used, the reagent can bind two or more analyte molecules. This method is appropriate for detecting analytes, such as those which can bind to only one construct molecule, which cannot be detected by the direct method. The presence of analyte in the sample is demonstrated by lack of or reduction in agglutination of particulates. The lack of or reduction in agglutination occurs because the analyte of interest in the sample inhibits the formation of ligating bonds between construct and reagent.

In either embodiment of the method of the present invention, the quantity of analyte of interest can be determined by relating or comparing the results obtained to a predetermined quantitative relationship between the extent of agglutination and the quantity or analyte of interest.

DIRECT METHOD OF ANALYSIS

In one embodiment of the present invention, referred to as the direct method, the presence and quantity of an analyte of interest are determined in a particulate-containing sample by admixing with the sample (e.g., whole blood) a construct which is capable of binding with both the analyte of interest and particulates present in the sample as obtained. Upon mixing of the construct with the sample, the following primary interactions occur among the primary (initial) reactants: analyte (A), particulates (P) and the construct (designated here p-a, which is the equivalent of a-p):

|      | Primary Reactants |         | Result of Interaction |
|------|-------------------|---------|------------------------|
| (1)  | P                 | + A     | No Reaction            |
| (2)  | p – a             | + p – a | No Reaction            |
| (3)  | P                 | + p – a | P~p – a                |
| (4)  | A                 | + a – p | p – a~A                |

As is evident, some of the primary interactions result in binding of the primary reactants (reactions (3) and (4)). These are referred to as primary binding events.

In addition, secondary interactions subsequently occur (once P~p-A and p-a~A have been formed). The secondary binding reactions occur while reactions (3) and (4) above are continuing. The following interactions are possible:

|      | Primary Reactant | Primary Product | Secondary Result      |
|------|------------------|-----------------|-----------------------|
| (5)  | P                | + P~p – a       | No Reaction or P2~p – a |
| (6)  | P                | + p – a~A       | P~p – a~A             |
| (7)  | A                | + P~p – a       | P~p – a~A             |
| (8)  | A                | + p – a~A       | No Reaction or p – a~A2 |
| (9)  | p – a            | + P~p – a       | a – p~P~p – a         |
| (10) | p – a            | + p – a~A       | p – a~A~a – p         |

As is evident here, too, some of the secondary interactions result in binding of the interacting materials and others do not. Those resulting in binding are referred to as secondary binding events or reactions.

Note that the product of reactions (6) and (7) is the same compound: P~p-a~A.

Higher-order binding reactions occur between the primary reactants and the various products of reactions (3)–(10). As a result of these higher order reactions, many complex species are formed via different possible reaction paths.

For reactions (3)–(10) and higher order reactions to occur, the primary reactants have the following properties:

(i) analyte (A) is capable of binding with at least two construct molecules, as in reaction (10);

(ii) particulates (P) are capable of binding with one or more construct molecules, as in reactions (3) and (9);

(iii) construct p-a is capable of binding to at least one analyte A and to at least one particulate P, as shown as (5) and (8).

The construct (p-a) used for the direct method is capable of binding with sample particulates and with the analyte of interest. Binding to both the particulates and the analyte occurs as a result of ligating bonds being formed between complementary binding sites and target sites. A useful construct, therefore, can be designed to be appropriate for the nature of the particulates and the analyte in the sample being analyzed. For example, the following possibilities exist:

(i) The analyte may have at least two identical binding sites; these sites may occur as an integral par of the analyte, in the absence of or in addition to other binding properties. In this case, the construct is designed to have target sites of this repeated site as shown in FIG. 4a and FIG. 4b.

(ii) The analyte may have at least two identical target sites, which may be present in the absence of or in addition to other binding properties. In this case, the construct is designed to have complementary binding sites (FIG. 4c and 4d).

(iii) The analyte may have one or more of each of two or more binding sites; these may occur in the absence of or in addition to other binding properties. In this case, the construct comprises a mixture of different molecules, each of which has a target site to one of the binding sites.

(iv) This case is as in (iii), except that the target sites are associated with the analyte and binding sites are used to form the construct mixture.

(v) In this case, the analyte may have both one or more binding sites and one or more target sites. The appropriate construct is a mixture of the complementary target sites and binding sites.

Identical situations as those described above (i–v) exist for the properties of particulates and the design and synthesis of a useful construct. In all, great flexibility in the design of the construct is provided.

The construct used in the present method must be able to bind to at least two particulates present in the sample as obtained. In some instances, the construct need bind to only one analyte molecule and in others, need bind to at least two analyte molecules; this is determined by the assay format used.

Construct is prepared by joining together two moieties, one which can bind with particulates and one which can bind with an analyte of interest. The present invention is not limited by the nature of the linkage joining the two moieties but such linking must be of sufficient strength to maintain the integrity of the construct when the construct is serving to link indicator particles to analyte via ligating bonds.

In the present invention, the presence and quantity of the analyte can be determined by detecting the occurrence of construct binding to both particulates and analyte in such a manner as to join at least two indicator particles. Any method that detects this binding will be usable in practicing the invention. For example, particle counting methods, such as impedance particle counting, can be used to detect the ligation of two or more indicator particles in the presence of analyte.

Use of the Direct Method for Immunoassay of Antibodies

The direct method of detecting and quantifying an analyte according to the present invention can be used in the analysis of, for example, aqueous solutions containing particulates and antibodies (the analyte). It can be used to analyze cell cultures of antibody-producing cells and is particularly useful for detecting and quantifying antibodies in samples of whole blood. The use of the direct method of the present invention is illustrated below through a description of detection of antibodies in whole blood. It is to be understood that this is not be to limiting in any way.

The construct for such an assay consists of linked moieties designed to form ligating bonds with: (1) indicator particles selected from the particulates known to be present in a whole blood sample as it is obtained (preferably cellular entities such as red blood cells, white blood cells, platelets) and (2) the analyte of interest (i.e., the antibody to be determined). The analyte to be detected is, for example, an immunoglobulin (i.e., a protein), such as IgG, IgM, IgE, IgA, IgD, etc.

The component of the construct which is to bind with particulates (e.g., red blood cells) is referred to here as the particulate-binding moiety. It is selected from a group of substances which have either (1) binding sites, such as those present in antibodies, lectins, etc., to target sites naturally present on surfaces of cells such as antigens, membrane structural components, etc.; or (2) target sites complementary to binding sites naturally present on cell surfaces.

The moiety of the construct which is to bind with the analyte of interest (here, an antibody) is referred to here as the analyte-binding moiety. The analyte-binding moiety is preferably an antigen or antigens specific for the antibody to be determined. It is also possible to use other substances which form ligating bonds with the analyte antibody, such as haptens, antigen analogs, homologs or antagonists, anti-idiotypic antibodies, anti-immunoglobulin antibodies etc.

The two moieties of the construct selected to serve as the particulate-binding moiety and the analyte-binding moiety are joined by means of covalent linking or other chemical means, known to the art, which result in their linking. For example, bifunctional reactive compounds may be employed in linking the moieties. Such bifunctional compounds contain reactive groups that form covalent or other stable bonds with chemical groups present on the moieties. Reactive groups such as aldehyde, maleimide, imidizolide, lactone, lactam, active ester, azide, acyl active hydrogen, unsaturated acyl, etc., have been found to be useful in the bifunctional compounds. Additionally, compounds such as carbodiimides, that activate functional groups (e.g., carboxyls), present on the component substances may be selected to synthesize the construct.

A method useful in determining the presence and quantity of antibody in a sample (e.g., whole blood), preferably comprises the following steps:

(1) obtaining a sample of whole blood in a manner such that clotting of the blood does not occur (e.g., by collecting the sample in heparin or other anticoagulant);

(2) mixing a volume of the blood sample with the construct. The construct will be either a solution (i.e., in water or other appropriate solvent) or a dry preparation;

(3) allowing the ligating reactions between the construct and the cellular components and between the construct and the analyte antibody, if present, to occur. This is accomplished by maintaining the combination formed in (2) under appropriate conditions (e.g., temperature, ionic strength, pH) for sufficient time for the reactions to occur;

(4) measuring or otherwise determining the extent of agglutination of blood cells by appropriate means, such as by visual detection, light scattering or absorption, particle counting or sizing, etc.;

(5) correlating the occurrence and degree of agglutination of the cells to the presence and quantity of analyte present. This can be done, for example, by reference to a pre-established standard curve.

It is an advantage of the present invention that known prior materials and techniques can be used to design and synthesize constructs and prepare reagents. Well-known techniques can also be used to carry out the analysis and read the results. These materials and techniques have been used, for example in immunoassay test reagents and immunoassays based on agglutination, enzyme immunoassay, radioimmunoassay, and fluorescent immunoassay. In presently-used immunoassay techniques for detecting antibodies in samples, the test reagent includes an antigen or antigens specific to the analyte antibody. These antigens may also be employed as the analyte-binding moiety of the construct of the present invention.

For example, a construct useful in the detection and quantification of antibody to rubella virus in human blood can comprise a particulate-binding moiety and a rubella-antibody-binding moiety joined together. The analyte-binding moiety useful in detecting antibody to rubella will be one or more antigens from rubella virus. Such antigens are well known and available; for example, they are presently used in commercial test kits for antibody to rubella which are available from Abbott Laboratories, Becton-Dickinson Company and Behring Diagnostics. Techniques used in preparing antigens from rubella virus for presently-used assays can be employed to prepare the analyte-binding moiety of the present invention.

In addition to the analyte-binding moiety, the construct of the present invention includes a particulate-binding moiety. In designing and synthesizing a construct useful for detecting antibodies in human blood, the particulate-binding moiety would preferably bind to red blood cells. The particulate-binding moiety can be selected from many substances (e.g., antibodies and lectins) that are known in the art. For example, rabbit antibody to sheep red cells are routinely employed for complement fixation tests, as described by Kabat in *Structural Concepts in Immunology and Immunochemistry*, pp 46–48 (1968). Lectins which form ligating bonds with red cells are commercially available from Sigma Chemical Co.; see, for example, 1986 Sigma Chemical catalog in which properties of lectins are presented and references are supplied.

When the method of the present invention is used to detect rubella antibodies in human blood, the particulate-binding moiety of the construct is selected from those substances capable of forming ligating bonds with human red blood cells; one particularly useful choice is one or more antibodies which bind human red blood cells. The particulate-binding moiety of the construct selected and used in a test for antibody to rubella may, of course, also be used in many other tests based on the present invention which use human red blood cells as indicator particles (e.g., hepatitis antibody antigens; bacterial antibodies, etc.

The construct of the invention is synthesized by joining the particulate-binding moiety to the analyte-binding moiety. There are numerous compounds and methods useful in joining two molecules together (while retaining the activity of each moiety) which are well known in the art. For example, enzyme immunoassays are made possible by joining antibodies to enzymes while retaining the activity of each substance. Such techniques have been used for example, in preparing reagents included in kits available from Syva Company, Abbott Laboratories and Cordis Laboratories. As explained previously, any method of linking or joining two materials which results in a connection or linkage with sufficient strength to maintain the construct integrity while the construct is in use (i.e., serving to link indicator particles to analyte). The necessary compounds and methods are well known in the art.

A construct useful in the rubella antibody test example is prepared by joining the particulate-binding moiety to the analyte-binding moiety. In this case, both moieties are proteins and, therefore, contain amino acid residues. Bifunctional linking compounds (e.g., commercially available with procedural documentation from Pierce Chemicals and others) react with the functional groups, such as hydroxyl, amino, thiol, and carboxyl groups of the proteins; this results in the two moieties being joined. The availability of asymmetric bifunctional linking compounds can be advantageously employed in the present invention to selectively join the two moieties into construct molecules. The construct molecules of the present invention will be of a molecular size and weight equal to the sum of the two moieties plus the linking compound; therefore, if necessary, they can be separated on the basis of their molecular size or weight from the unlinked moieties. This can be done, for example through the use of processes such as gel filtration chromatography (available from Pharmacia Fine Chemicals) electrophoresis and controlled pore size membrane filtration.

A reagent useful in detecting antibody to rubella can be prepared using the construct prepared to react with human red blood cells and with antibody to rubella virus antigens. The concentration of the construct in the reagent is selected so that: 1) in the absence of the analyte antibody (e.g., as is the case in known negative samples), no detectable agglutination of the red blood cells of the sample occurs and 2) in the presence of the analyte antibody, detectable agglutination occurs. An appropriate concentration of the construct to be used is selected and mixed in a solution of salts (e.g., NaCl, KCl, etc.) and pH buffers (e.g., phosphates, TRIS, HEPES, etc.) and other chemicals commonly used in commercially available test reagents. Such a mixture thus includes not only the construct, as the active ingredient, but also other ingredients which preserve the activity of the construct during storage and control the optimum reaction conditions of pH, ionic strength, etc., of the reaction mixture.

An example of a method of detecting antibodies to rubella virus antigens may include the following steps:

(1) drawing human whole blood samples into an anticoagulant, such as heparin or EDTA, as is the current practice for cytology and hematology samples;

(2) mixing a small volume of blood (e.g., as little as 1 microliter but generally about 20 microliters or more) with a prescribed volume of the reagent (e.g., 100 microliters);

(3) maintaining the reaction mixture at room temperature sufficient time for agglutination to occur (e.g., several minutes); and (4) determining the presence or absence of antibody to rubella by visually detecting the presence or absence of agglutination of the red cells.

A reagent and method to detect antibodies to rubella in laboratories equipped with cell counters, such as those available from Coulter Electronics, differs from that described above in the concentration of the construct, which is selected to allow detection of the analyte antibody through measurement of agglutination on these instruments.

The present invention can be used for other antibodies in human blood samples as described above for rubella; in each case, one or more antigens specific for the analyte antibody of interest is included in the construct to be used. For example, an AIDS test can be prepared by employing HIV antigens, either as obtained from HIV virus or genetically engineered, (e.g., those presently used in tests available from Abbott Laboratories, Electronucleonics, Inc.) as the analyte-binding moiety and selecting the concentration of the construct to meet the requirements of AIDS testing.

It is a feature of the present invention that the blood of any species that contains red blood cells, or the semen of any species containing sperm cells, can be tested. For example, tests for antibodies in animal blood, such as trichina antibodies in hog blood, can be provided. The particulate-binding moiety of the construct is selected from substances that form ligating bonds with the cells of the species of interest. For particulates such as red blood cells and sperm cells, lectins are especially useful as the particulate binding moiety. Potentially any lectin can be used and the preferred lectin for a selected particulate can be determined empirically as described herein.

As shown specifically in Examples I and V, when the method of the present invention is used to detect an analyte of interest in equine or feline blood, a particularly useful particulate-binding moiety is the lectin phytohemagglutinin. When used to detect an analyte in bovine blood, as shown in Example IV, a particularly useful particulate-binding moiety is the lectin WGA (wheat germ).

The present method has been used to detect endotoxin in whole blood obtained from horses (See Example II). Endotoxin is a ubiquitous constituent of the cell wall of gram-negative bacteria and is released from the microbial cell wall when a bacterium dies or is undergoing rapid cell division. When endotoxin enters the blood of an infected individual or animal, the result is endotoxemia, which is a serious complication of many human and animal diseases. For example, endotoxemia is often a serious complication of equine colic. Presently available methods of diagnosing endotoxemia (e.g., assessing clinical symptoms, endotoxin determination using Limulus amebocyte lysate and hematological studies do not provide reliable, reproducible results and are not suited for use in the field. As described below, a two-component construct has been developed which is useful in detecting and/or quantitating endotoxin in whole blood samples. The construct includes one moiety which binds to a particulate (e.g., erythrocytes or RBC) present in whole blood as it is obtained from an animal or individual and one moiety (referred to as the endotoxin binding moiety or EBM) which binds selectively to endotoxin. The presence of endotoxin in a whole blood sample inhibits erythro-agglutination; in the presence of endotoxin, binding between EBM and endotoxin occurs, resulting in steric hindrance of the binding sites of PHA and, thus in inhibition of erythro-agglutination.

Briefly, the method of detecting endotoxin level is carried out as follows: Blood is obtained (e.g., by venipuncture), using known techniques, and treated to prevent coagulation (e.g., by drawing the blood into an anticoagulant, such as heparin or EDTA). The blood is diluted, if necessary, to an appropriate concentration (e.g., by combining it with an appropriate buffer, such as PBS), and some or all of the diluted sample is combined with the construct. The resulting sample-construct combination is maintained under conditions (e.g., temperature, sufficient time, with agitation if needed) appropriate for agglutination of the sample to occur; a control, which includes a sample of the blood, the endotoxin-binding moiety of the construct and the reagent (the construct in PBS containing BSA), was assessed for agglutination under the same conditions. The time necessary for agglutination of the sample being analyzed is compared with the time necessary for agglutination of the control. Alternatively, the time necessary for agglutination of cells to occur can be correlated with a predetermined relationship between time for agglutination and the quantity of endotoxin present determined. Thus, the endotoxin concentration of a sample can also be determined. The extent to which agglutination occurs is determined using known means, such as visual detection, light scattering or absorption, or particle counting or sizing.

In one embodiment of the present method, endotoxin is detected in whole blood from an animal, such as a horse as follows: A whole blood sample is drawn into a test tube containing heparin or EDTA. A small quantity of the whole blood is diluted (1:3) in PBS and combined with a construct in which the two covalently-bound moieties are the lectin phytohemagglutinin (PHA) from *Phaseolus vulgaris* (as the aldehyde prepared as described in Example I), which binds red blood cells, and polymyxin B, an antibiotic known to bind to endotoxins from gram-negative bacteria.

The sample and the construct are combined on a slide or in a well and the resulting combination is maintained at room temperature until agglutination occurs or until a set length of time (e.g., 3 minutes) has passed. During this time, combination can be rotated to mix the components. A control, which is made up of the diluted blood sample, reagent and polymyxin B, is run at the same time and processed in the same way as the test sample. Agglutination of the sample being tested and of the control is determined visually (e.g., by unaided eye); if agglutination is not detectable within the set length of time, it is assumed that it will not occur (indicating that the sample contains endotoxin in sufficient quantity to prevent agglutination). As shown in Table 1, the present method and the PHA-aldehyde/polymyxin B construct have been used to demonstrate endotoxin levels in whole blood from horses with a variety of clinical diagnoses. In each case in which endotoxin level, as assessed using presently-available methods (e.g., assessment of clinical symptoms) was elevated, agglutination of the sample was inhibited (i.e., occurred more slowly than agglutination of the control or occurred to a lesser extent than was evident in the control in the same length of time).

The construct described above includes two moieties, each of which binds specifically to a selected partner. Other constructs in which each of the two moieties has the same selective binding ability (i.e., to bind RBC and endotoxin, respectively) can also be used. For example, antibodies to equine red blood cells or to core region of endotoxin can be used. Similarly, other constructs in which one moiety binds RBC present in a whole blood sample as it is obtained and one moiety binds a product characteristic of an organism to be detected in blood (e.g., endotoxins) can also be produced and used in the present method.

In addition, particulate-containing samples, other than whole blood, can be used. By way of example, antibody can be detected in an in vitro culture of monoclonal antibody-secreting hybridoma cells. In these instances, the construct can be synthesized from a particulate-binding moiety that binds to, for example, mouse-mouse hybridoma cells, and an analyte-binding moiety specific for the antibody being produced.

An example of the use of the method of the present invention to detect an analyte in a particulate containing sample other than whole blood is shown in Example III. Specifically, constructs useful for the detection of an analyte of interest in equine semen can be prepared in which sperm cells serve as the particulate and the particulate binding moiety is selected from a group of lectins which includes SJA (Pagoda Tree), VFA (Fava Bean), and PHA (Red Kidney Bean).

The constructs described can be modified as needed to detect other analytes of interest and the constructs and their uses described above are not intended to be limiting in any way.

Use of the Direct Method for Immunoassay for Antigens

The direct method can also be used to detect and quantify antigens in a sample, such as whole blood. The method used below is similar to that previously described for antibody detection and quantification.

This embodiment differs from the previously described method for antibodies, however, in the analyte-binding substance that is one moiety of the construct. The construct used can be prepared from, for example, antibody or antibody fragments (e.g., Fab') which bind to cells present in the sample, and from antibody or antibody fragments which are reactive with the antigen to be determined. The antigen to be determined must be comprised of two or more target sites that react with the binding sites provided in the construct. The method of determination of the antigen will be the same as the assay for antibody described above.

For example, a test for hepatitis B surface antigen (HBsAg) in human blood can be carried out using a construct comprising (1) a particulate binding moiety, as described above with reference to rubella antibody and (2) an analyte-binding moiety selected from those substances, such as antibodies, known to bind to HBsAg. Antibodies to HBsAg which can be used are, for example, those presently used in commercially-available tests from Abbott Laboratories and Cordis Laboratories, and others. The antibodies can be of human or non-human origin. These two moieties, each containing functional groups of amino acid residues, are joined to form the construct, as described above in relation to the rubella antibody.

Similarly, tests for other antigens in human and non-human blood can be provided by employing specific antibodies or antibody fragments as the analyte-binding moiety of the construct. The reagent preparation and test methods are as described previously for antibody testing.

Use of the Direct Method for Non-Immunoassays for Substances

The direct method of the present invention, as described previously for use in determining antibodies or antigens can also be practiced for determining the presence of other substances (analytes) in a sample. The direct method is applicable to detection of analytes that have at least two binding sites or target sites, in samples which contain particulates that can bind with a construct.

For example, the method may be used to detect the presence and determine the quantity of receptors, binding proteins, carrier molecules, sequestering compounds, and other molecules or aggregates of molecules that form ligating bonds with hormones, activators, agonists, antagonists, inhibitors, substrates, cofactors, and molecules that contain two or more target sites. This can be done by using an appropriately-designed construct for the analyte to be determined; in this case the construct is designed to have binding activity complementary to that of the analyte.

The method of the present invention can also be practiced on samples other than human or animal blood samples. For example, it can be used to analyze samples which contain cells (e.g., samples obtained from microbial fermentation, tissue culture, etc.), by utilizing the cells that are present in the sample as the indicator particles.

By way of example, a construct useful in detecting active avidin in chicken blood will have a particulate-binding moiety that binds chicken red blood cells to which biotin, the analyte-binding moiety is joined. Any of the commercially available biotin derivatives, such as d-biotin-N-Hydroxysuccinimide ester available from Sigma Chemical Company, may be used to form the construct. Using this construct in the reagent, agglutination of the red blood cells will occur only when avidin, which has four biotin binding sites, is present in an active form capable of binding two or more biotin molecules present in the construct. An immunoassay for avidin, by contrast, would detect antigenically active avidin and, therefore, would not provide information on biotin binding activity in the blood.

Use of the Direct Method to Determine Particulate Associated Substances

The method and construct of the present invention can also be used to detect the presence and quantity of binding sites or target sites on the surfaces of cells, in a sample containing two or more types of particulates (e.g., whole blood). For example, the method may be useful for determining the presence and quantity of a specific type of cell (e.g., white cells, lymphocytes, basophiles, B-cells, infected cells, microbial cells, activated cells, immature cells, etc.) in the presence of another type of cell (e.g., red blood cells) in whole blood. The construct used is designed to form ligating bonds with both the analyte (which in this case is particulate) and the indicator cell type (which is a second, different particulate).

The ability to test for substances in whole blood using the present invention is particularly valuable in detecting cells or cell-associated analytes. For example, reagents are presently available from Ortho Diagnostics to perform T and B cell classification of human white blood cells. These tests require, in addition to the cell type specific antibodies, expensive instrumentation run by highly trained personnel. It is an object of the present invention to provide a construct comprising a moiety that will bind to human red cells joined to antibodies currently used to classify white cells. Due to the difference in relative concentration between red cells and white cells in human blood (5 million red cells compared to 4 to 10 thousand white cells per microliter), white cells of the type selected for by the analyte-binding moiety of the construct will be easily detectable, for example by microscopy, due to the presence of bound red cells.

In addition, the presence of bacterial cells in blood, either directly or after culture, can be detected by using analyte-binding moiety of the construct which binds to the bacteria of interest. For example, antibodies against the bacterial species may be employed. Alternatively, penicillin derivatives can serve as the analyte-binding moiety to detect the presence of bacteria that have penicillin-binding proteins as a component of their cell walls.

INDIRECT METHOD OF ANALYSIS

A second embodiment of the present invention, referred to as the indirect method, is useful in detecting analytes which cannot be detected by the direct method, as is the case when an analyte can bind to only one construct molecule. It is possible to detect such analytes by using two compositions: 1) a construct and 2) a reagent. In this method the particulate-binding moiety of the construct is the same as that described for the direct method.

In one application of the indirect method, the analyte-binding moiety is a component of the construct (as is the case, as described above, for the direct method) and the reagent is two or more analyte entities joined together and capable of binding two or more construct molecules.

In a second application of the indirect method, two or more analyte-binding moieties (e.g., an antibody specific for the analyte of interest), joined together, comprise the reagent. The construct in this case is the analyte, bound to the particulate-binding moiety. This application is illustrated in Example II.

Use of either of the two applications of the indirect method results in inhibition of agglutination of analyte is present. In either case, inhibition may be partial or complete, depending on the relative amounts of analyte and reagent present.

This embodiment of the present invention can be used to detect the presence and quantity of a substance which has a single, non-repeated target site or which can bind only one construct containing a target site. This is useful, for example, in analyzing samples for substances such as haptens, steroid hormones, low molecular weight drugs (typically having a molecular weight of less than 1,000), antibiotics, and binding proteins. If the method is used to detect and quantitate substances with monovalent binding properties, the following occurs: a construct which binds to the analyte and to the indicator B particles in the sample is added to the sample; a polymeric form of the analyte entity is also added. If analyte is present in the sample, agglutination or clumping of the indicator particles is inhibited because the reagent competes with the analyte for binding to the construct. The result is reduction in the degree of clumping, which can be partial or complete inhibition of agglutination. Inhibition of agglutination is indicative of the presence of the analyte; the degree of inhibition is indicative of the quantity of the analyte in the sample.

The indirect method can rely on any of a variety of binding reactions, as described for the direct method. It can also be formatted to allow for, in addition to inhibition of clumping, reversal of clumping.

Examples of tests that can be performed using the indirect method include those known in the art of hapten assays. Included in this class are therapeutic drug monitoring tests, such as gentamicin, digoxin, phenobarbitol, phenytoin, and hormone tests, such as thyroxin, estrogen, cortisol. For example, a construct useful in a test for digoxin as the analyte in human blood would comprise a particulate-binding moiety (such as described above in relation to testing for rubella antibody) joined to the antibody to digoxin by methods previously discussed. Due to the nature of digoxin, in this instance, and haptens as a general class, the analyte can form a ligating bond with one and only one construct molecule.

It is an advantage of the present invention that by providing a reagent in addition to the construct, tests useful for detecting haptens can be performed. The reagent in the present example can comprise an oligomeric or a polymeric form of digoxin which can be prepared, for example, by: (1) specifically oxidizing the vicinal glycols present in digoxin to aldehydes using periodic acid; (2) mixing the oxidized digoxin with a suitable polymer containing a plurality of amino groups, such as human serum albumin or poly-lysine, to allow the formation of imine bonds between the aldehyde and amino groups; and (3) reducing the imines so formed to secondary amines linking digoxin to the polyamine with sodium cyanoborohydrate. These and similar reactions are commonly practiced in modifying haptens to impart antigenicity. These techniques can be employed in preparing oligomeric and polymeric forms of haptens other than digoxin.

Use of the indirect method of the present invention to test for haptens, such as digoxin, makes use of two reagents. A construct is prepared, as previously described, wherein the analyte-binding moiety specifically binds digoxin. In this case, however, agglutination of the red cells present in the sample occurs only in the presence of a reagent which is the polymerized analyte (here, digoxin). In this instance, the concentration of the construct and of the polymerized digoxin are selected such that when the sample is combined with the construct and the reagent, agglutination of the red cells occurs in the absence of analyte digoxin; in the presence of digoxin at clinically significant concentrations, detectable inhibition of agglutination occurs.

It is a particular advantage of the present invention that the breadth of applicability to a variety of analytes in a variety of samples described for the direct method embodiment is comparably broad using the indirect method due to the similar function performed by the construct in the two methods.

The present invention will now be illustrated by the following examples, which are not to be seen as limiting in any way.

EXAMPLE I

Equine Whole Blood Immunoassay for Analytes

A. Lectin Indicator-Particle Binding Moiety

Anticoagulated equine blood samples were collected by jugular venipuncture. The blood was drawn into Vacutainer blood collection tubes (Becton Dickinson Vacutainer Systems) containing EDTA or heparin. The blood was thoroughly mixed with the anticoagulant and stored at 2°–8° C. until tested.

The lectin phytohemmagglutinin from *Phaseolus vulgaris* (PHA), purchased from Sigma Chemical Company, was reconstituted in normal saline to 5 mg/mL. Dilutions of PHA were made in pH 7.4 Tris buffered saline containing 0.5 mg/mL bovine serum albumin (Tris-saline-BSA). Each dilution of PHA in Tris-saline-BSA was tested for agglutination with equine blood diluted 1:3 in the same buffer. To test for agglutination, 15 microliters of diluted blood and 15 microliters of PHA solution were mixed on a plastic sheet and rotated. Time of agglutination was recorded for all tests where agglutination was observed within 240 seconds of mixing. Any mixture that failed to produce agglutination within 240 seconds was considered to be negative. Agglutination of RBCs occurred with PHA at concentrations above 1.2 micrograms/mL of PHA. At PHA concentrations above 7 micrograms/mL, maximum agglutination was observed to occur instantaneously upon mixing. By plotting the reciprocal of PHA concentration against time to agglutination for the concentration range of PHA from 1.0 to 5.0 micrograms/mL, a linear relationship was obtained. These results indicated that the concentration of an agglutinin (PHA) can be determined by measuring the time of agglutination and comparing the results with a standard curve.

The lectin PHA was used as the indicator particle binding moiety to prepare constructs to bind to equine RBCs, the latter being the selected indicator particle in the assays.

B. Purification of the Lectin PHA

PHA (protein form) was purified from *Phaseolus vulgaris* (red kidney beans) by the method of Rigas and Osgood. *J. Biol. Chem.* 212:607–615 (1955). Approximately 2 grams of PHA were obtained from 1 kgm of dried beans. Electrophoretic analysis of purified PHA by SDS-PAGE showed one major band which was stained for protein using Coomassie Brilliant Blue R and also stained for carbohydrate by Periodic Acid-Schiff's. The PHA thus purified was dissolved in saline and used to prepare constructs.

C. Preparation of PHA-aldehyde

Constructs were prepared with PHA as the indicator particle binding moiety. PHA-aldehyde was synthesized by oxidizing PHA by adding a 150 molar excess of $NaIO_4$ in saline at 2°–8° C. for 1–24 hours. To prepare PHA-aldehyde, 2.46 mL of 100 mM $NaIO_4$ was added to 14.0 mL of PHA, 14.1 mg/mL in saline, and the reaction mixture was incubated overnight at 4° C. The presence of aldehyde groups was confirmed by a positive reaction with Schiff's reagent.

EXAMPLE II

Assay for Bacterial Endotoxin in Equine Blood

Endotoxin, a ubiquitous constituent of the cell wall of gram-negative bacteria, is released from the microbial cell wall at death of the bacterium. When endotoxin enters the blood, endotoxemia results and is a serious complication in many human and animal diseases.

A. Preparation of Constructs

Constructs for an equine endotoxin test were prepared from PHA-aldehyde from Example I and polymyxin B, an antibiotic known to bind to endotoxins from many species of gram-negative bacteria. Polymyxin B (from Sigma Chemical Company or other commercial sources) has multiple amino groups that are used in forming the constructs by condensation with aldehyde functions of PHA-aldehyde. The resultant imine bonds are reduced to secondary amines that result in PHA and polymyxin B being covalently bonded into constructs.

By way of example, 2 mL of PHA-aldehyde, 1.3 mg/mL in saline, and 0.025 mL of 13.5 mM polymyxin B in water were mixed and incubated overnight at 4° C. $NaCNBH_3$, 0.025 mL of a 90 mM solution, was added and incubated for 30 minutes at room temperature. The construct was precipitated with 80% saturated ammonium sulphate; collected by centrifugation at 8,000 ×g for 35 minutes; and dissolved in acetate-saline pH 5.5 to approximately 1 mL.

B. Detection of Endotoxin in Equine Blood

The endoxotin test is performed by adding 50 uL of whole blood (drawn from the jugular vein) diluted 1:3 in PBS to 50 uL of construct. The mixture is rotated on a slide for 3 minutes or until agglutination is observed. PHA-polymyxin B construct was diluted in pH 7.4 PBS containing 0.5 mg/mL BSA to a concentration that resulted in agglutination of equine RBC in normal blood in 60–75 seconds. Construct at that dilution was prepared as the reagent. The control was prepared by adding polymyxin B to a portion of the reagent to a final concentration of 0.1 mM.

Results are obtained by comparing time to agglutinate with the reagent to that of the control. The difference in the agglutination times is directly proportional to the level of endotoxin present in the blood and gives a semiquantitative measurement of endotoxin level.

TABLE 1

Detection of Endotoxin in Equine Blood and Correlation with Clinical Assessment

| Diagnosis | Sample | Endotoxin Level | Comments |
|---|---|---|---|
| Nephro-Splen | Post-Sx | Pos. | 15–20 sec. |
| Entrapment | 48 h | High Pos. | 20–30 sec. |
| Impaction | 72 h | Pos. | 15–20 sec. |
|  | 78 h | Pos. | 15–20 sec. |
|  | 87 h | High Pos. | 20–30 sec. |
|  | 91 h | High Pos. | 20–30 sec. |
| Ant. Enteritis | Pre-Sx | High Pos. | 20–30 sec. |
|  | Post-Sx | High Pos. | 20–30 sec. |
|  | 6 h Conval. | Neg. | <5 sec. |
|  | 12 h Conval. | +/− | 5–10 sec. |
|  | 21 h Conval. | Low Pos. | 10–15 sec. |
|  | 27 h Conval. | Low Pos. | 10–15 sec. |
| Colonic Torsion | Pre-Sx | Pos. | 15–20 sec. |
| No Resection | Post-Sx | High Pos. | 20–30 sec. |
|  | 2 h Conval. | High Pos. | 20–30 sec. |
|  | 6 h Conval. | Pos. | 15–20 sec. |
|  | 12 h Conval. | Pos. | 15–20 sec. |
|  | 21 h Conval. | +/− | 5–10 sec. |
|  | 26 h Conval. | +/− | 5–10 sec. |
| Diarrhea | 3 d Conval. | Pos. | 15–20 sec. |
| Verm. Colic | 6 h Post-Ad. | High Pos. | 20–30 sec. |
|  | 15 h Post-Ad. | High Pos. | 20–30 sec. |
|  | 21 h Post-Ad. | High Pos. | 20–30 sec. |
| Colon Tumors | Pre-Sx | Pos. | 15–20 sec. |
| Ant. Enteritis | Admin. | High Pos. | 20–30 sec. |
| Scrotal Hernia | Pre-Sx | Neg. | <5 sec. |
|  | Post-Sx | Pos. | 15–20 sec. |
|  | 5 d Conval. | Low Pos. | 10–15 sec. |
|  | 11 d Conval. | Low Pos. | 10–15 sec. |
| Jejunum Resect. | Post-Sx | Neg. | <5 sec. |
| Colonic Torsion | Pre-Sx | Very High | >35 sec. |
| S. I. Volvu. | Post-Sx | Neg. | <5 sec. |
| Septic Periton. | 14 d Conval. | Neg. | <5 sec. |
| S. I. Impact |  | Low Pos. | 10–15 sec. |
| Ant. Enteritis |  | +/− | 5–10 sec. |
| S. I. Adhes. | Post-Sx | Neg. | <5 sec. |
| Sm. Colon Rupt. |  | Very High | >60 sec. |
| Colonic Enterolith |  | Very High | >30 sec. |
| Enterolith | Post-Sx | +/− | 5–10 sec. |
| Impaction | Post-Sx | Low Pos. | 10–15 sec. |
|  | Pre-Euth | Pos. | 15–20 sec. |

Post-Sx = Post surgery
Ant. Enteritis = Anterior Enteritis
Pre-Sx = Pre surgery
Verm. Colic = Verminus Colis
Septic Periton. = Septic Peritonitis
Jejunum Resect. = Jejunum Resection
S. I. = Small Intestine
Adhes. = Adhesion

EXAMPLE III

Selecting Indicator-Particle Binding Moieties for Equine Semen

Semen was collected from stallions, filtered to remove the gel fraction and extended in skim milk extender to a concentration of 50 million sperm cells/mL. To 100 microliters of extended semen, 20 microliters of lectin solution at 0.5 mg/mL was added. The mixtures were incubated for at least 1 minute at room temperature and 20 microliters of the mixture was placed on glass microscope slide and examined for agglutination of sperm cells at 45× with a dissecting microscope. Table 2 describes the lectins tested and the results obtained.

TABLE 2

| Lectin | Agglutination Result |
|---|---|
| BS-1 (Griffonia) | Negative |
| SBA (Soybean) | Negative |
| LBL (Lima Bean) | Negative |
| SJA (Pagoda Tree) | Weak Positive |
| WGA (Wheat Germ) | Negative |
| UEA-1 (*Ulex europaeus*) | Negative |
| VFA (Fava Bean) | Positive |
| PHA-P (Red Kidney Bean) | Strong Positive |
| PWM (Pokeweed) | Negative |
| Control Saline | Negative |

From these data, it was concluded that SJA, VFA and PHA are useful as indicator particle binding moieties in preparing constructs to perform assays for analytes in equine semen.

EXAMPLE IV

Selecting Indicator-Particle Binding Moieties for Bovine Blood

The procedure described in Example III for selection of indicator-particle binding moieties for equine semen was performed using bovine blood collected in an equal volume of anticoagulant solution, such as Alsever solution, diluted 1:1.5 in tris-saline. The lectins described in Example III were tested, at the concentrations described in that example. The lectin WGA (*Triticum vulgaris*, wheat germ) was shown to agglutinate bovine RBCs.

EXAMPLE V

Selective Indicator-Particle Binding Moieties for Feline Blood

The procedure described in Example III for selection of indicator-particle binding moieties for equine semen was performed using feline blood collected in EDTA or citrate vacutainer blood collection tubes diluted 1:3 in tris-saline. The lectin PHA was tested at 0.5 mg/mL, as described in Example I and was shown to agglutinate feline RBCs.

Equivalents

Those skilled in the art will recognize, or be able to ascertain using no more than routine experimentation, many equivalents to the specific embodiments of the invention described herein. Such equivalents are intended to be encompassed by the following claims.

I claim:

1. A method of determining an analyte of interest in a semen sample, comprising the steps of:
   a) contacting the semen sample with a construct comprised of a first moiety which binds to sperm cells present in the sample as obtained and a second moiety which binds to the analyte of interest, under conditions appropriate for binding of sperm cells to the first moiety of the construct and binding of analyte of interest to the second moiety of the construct; and
   b) detecting agglutination of sperm cells in the sample after contacting the sample with the construct of step (a).

2. The method of claim 1 wherein the first moiety is a lectin.

3. A method of claim 2, wherein the first moiety is a lectin selected from the group consisting of: phytohemagglutinin, Pagoda tree lectin and Fava bean lectin.

4. The method of claim 2, wherein the first moiety is an antibody.

5. A method of claim 2, wherein the semen sample is of equine origin.

6. A composition for detecting endotoxin in whole blood, comprising a construct consisting essentially of two moieties joined together: a first moiety which is a lectin which binds red blood cells present in the sample as obtained, but not to the analyte of interest and a second moiety which is polymyxin B, wherein the construct is capable of agglutinating red blood cells in the sample in the absence of endotoxin, and wherein, following addition of the construct to the sample, the presence of endotoxin in the sample leads to a decrease in the time required for agglutination or in the extent of agglutination at a selected time as compared to an appropriately-selected control.

7. A method of determining endotoxin in a particulate-containing sample, comprising the steps of:
   a) contacting the sample with a construct comprised of a first moiety which is a lectin having binding specificity for particulates present in the sample as obtained, but not for endotoxin, and a second moiety which is polymyxin B, under conditions appropriate for binding of particulate to the first moiety of the construct and binding of endotoxin to the second moiety of the construct, wherein binding of the particulate in the sample to the lectin results in agglutination and the presence of endotoxin in the sample inhibits agglutination; and
   b) detecting agglutination of particulates in the sample after contacting the sample with the construct of step (a),
   whereby inhibition of agglutination is observed in the presence of endotoxin.

8. The method of claim 7 wherein the particulate-containing sample is selected from the group consisting of whole blood and semen.

9. The method of claim 8 wherein the particulate-containing sample is selected from the group consisting of: equine whole blood, feline whole blood and equine semen, and the lectin is phytohemagglutinin.

10. The method of claim 8 wherein the particulate-containing sample is bovine whole blood and the first moiety is the lectin wheat germ agglutinin.

11. The method of claim 8 wherein the particulate-containing sample is equine semen and the first moiety is a lectin selected from the group consisting of: phytohemagglutinin, Pagoda tree lectin and Fava bean lectin.

12. A method of determining endotoxin in an equine whole blood sample, comprising the steps of:
   a) contacting the whole blood sample with a construct comprised of a first moiety which is a lectin which binds specifically to red blood cells present in the whole blood sample as obtained, but not to endotoxin, and a second moiety which is polymyxin B, under conditions appropriate for binding of red blood cells to the first moiety of the construct and binding of endotoxin to the second moiety of the construct; and
   b) determining the extent to which agglutination of the whole blood sample occurs, wherein inhibition of agglutination is indicative of the presence of endotoxin in the whole blood sample.

13. The method of claim 12 wherein the first moiety is the lectin phytohemagglutinin.

14. The method of claim 12 wherein in step (b), the extent to which agglutination of the whole blood sample occurs is determined by measuring the time necessary for agglutination of the whole blood sample to occur.

15. The method of claim 14, further comprising comparing the time necessary for agglutination of the whole blood sample to occur with the time necessary for agglutination of an appropriately-selected control to occur.

16. The method of claim 15 wherein the level of endotoxin present in the equine whole blood sample is determined by comparing:
   (a) the difference between
      (1) the time necessary for agglutination of the whole blood sample; and
      (2) the time necessary for agglutination of the appropriately-selected control; with
   (b) a predetermined relationship between the difference and endotoxin levels in equine whole blood.

17. A method of determining endotoxin in a semen sample, comprising the steps of:
   a) contacting the semen sample with a construct comprised of a first moiety which binds to sperm cells present in the sample as obtained and a second moiety which is polymyxin B, under conditions appropriate for binding of sperm cells to the first moiety of the construct and binding of endotoxin to the second moiety of the construct, wherein binding of sperm cells in the sample to the first moiety results in agglutination of sperm cells and the presence of endotoxin in the sample inhibits agglutination of sperm cells; and
   b) detecting agglutination of sperm cells in the sample after contacting the sample with the construct of step (a),
   whereby inhibition of agglutination is observed in the presence of endotoxin.

18. The method of claim 17, wherein the first moiety is a lectin.

19. The method of claim 18, wherein the first moiety is a lectin selected from the group consisting of: phytohemagglutinin, Pagoda tree lectin and Fava bean lectin.

20. The method of claim 18, wherein the semen sample is of equine origin.

21. The method of claim 17 wherein the first moiety is an antibody.

22. A construct for detecting endotoxin in a whole blood sample, consisting essentially of two moieties joined together: a first moiety which is a lectin which binds red blood cells, but not endotoxin, and a second moiety which is polymyxin B, wherein the construct is capable of agglutinating red blood cells in the sample in the absence of endotoxin, and wherein the presence of endotoxin in the sample leads to a decrease in the time required for agglutination or in the extent of agglutination at a selected time following addition of the construct to the sample as compared to an appropriately-selected control.

23. The construct of claim 22, wherein the red blood cells are of equine or feline origin and the first moiety is the lectin phytohemagglutinin.

24. The construct of claim 22, wherein the red blood cells are of bovine origin and the first moiety is the lectin wheat germ agglutinin.

25. A composition for determining endotoxin in a whole blood sample, comprising a construct comprising two moieties joined together: a first moiety which is a lectin which binds red blood cells present in the whole blood sample as obtained, but not to endotoxin, and a second moiety which is polymyxin B, wherein the construct is capable of agglutinating red blood cells in the sample in the absence of endotoxin, and wherein, following addition of the construct to the sample, the presence of endotoxin in the sample leads to a decrease in the time required for agglutination or in the extent of agglutination at a selected time as compared to an appropriately-selected control.

26. The composition of claim 25 wherein the first moiety is the lectin phytohemagglutinin.

27. A kit for determining endotoxin in a whole blood sample comprising a construct and an appropriate solvent, the construct comprising two moieties joined together: a first moiety which is a lectin which binds to red blood cells, but not to the analyte of interest, and a second moiety which is polymyxin B, wherein the construct is capable of agglutinating red blood cells in the sample in the absence of endotoxin, and wherein, following addition of the construct to the sample, the presence of endotoxin in the sample leads to a decrease in the time required for agglutination or in the extent of agglutination at a selected time as compared to an appropriately-selected control.

28. The kit of claim 27 wherein the lectin is phytohemagglutinin.

29. A construct for determining endotoxin in semen, comprising two moieties joined together: a first moiety which is a lectin which binds to selected particulates present in semen as obtained, but not to endotoxin, and a second moiety which is polymyxin B, wherein the construct is capable of agglutinating the selected particulates present in the sample in the absence of endotoxin, and wherein, following addition of the construct to the sample, the presence of endotoxin in the sample leads to a decrease in the time required for agglutination or in the extent of agglutination at a selected time as compared to an appropriately-selected control.

30. The construct of claim 29 wherein the semen is equine semen and the lectin is selected from the group consisting of: phytohemagglutinin, Pagoda tree lectin, and Fava bean lectin.

31. A construct for detecting endotoxin in a semen sample, comprising a first moiety which is a lectin which binds to sperm cells, but not to endotoxin, and a second moiety which is polymyxin B, wherein the construct is capable of agglutinating sperm in the absence of endotoxin, and wherein, following addition of the construct to the sample, the presence of the endotoxin in the sample leads to a decrease in the time required for agglutination or in the extent of agglutination at a selected time as compared to an appropriately-selected control.

32. The construct of claim 31 wherein the lectin moiety is selected from the group consisting of: phytohemagglutinin, Pagoda tree lectin, and Fava bean lectin.

33. A kit for detecting endotoxin in a semen sample comprising a construct and an appropriate solvent, said construct comprising a first moiety which is a lectin which binds to sperm cells, but not to endotoxin, and a second moiety which is polymyxin B, wherein the construct is capable of agglutinating sperm in the absence of endotoxin, and wherein, following addition of the construct to the sample, the presence of endotoxin in the sample leads to a decrease in the time required for agglutination or in the extent of agglutination at a selected time as compared to an appropriately-selected control.

34. A method of detecting endotoxin in a whole blood sample, comprising the steps of:

a) contacting the whole blood sample with a construct comprised of a first moiety which is a lectin and which binds specifically to red blood cells present in the sample as obtained, and a second moiety which is polymyxin B, under conditions appropriate for binding of red blood cells to the first moiety of the construct and binding of endotoxin to the second moiety, wherein binding of red blood cells in the sample to the first moiety results in agglutination of red blood cells and the presence of endotoxin in the sample inhibits agglutination of red blood cells; and b) detecting agglutination of the whole blood sample, whereby inhibition of agglutination is observed in the presence of endotoxin.

35. The method of claim 34 wherein the lectin is phytohemagglutinin.

36. The method of claim 35 wherein in step (b), the extent to which agglutination of the whole blood sample occurs is determined by measuring the time necessary for agglutination of the whole blood sample to occur.

37. The method of claim 36, further comprising comparing the time necessary for agglutination of the whole blood sample to occur with the time necessary for agglutination of an appropriately-selected control to occur.

38. The method of claim 37, wherein the level of endotoxin present in the whole blood sample is determined by comparing:

a) the difference between
(1) the time necessary for agglutination of the whole blood sample; and
(2) the time necessary for agglutination of the appropriately-selected control; with b) a predetermined relationship between the difference and endotoxin levels in whole blood.

39. A construct for detecting endotoxin in a whole blood sample comprising two moieties joined together: a first moiety which is a lectin and which binds specifically to red blood cells present in the sample as obtained, but not to endotoxin, and a second moiety which is polymyxin B, wherein the construct is capable of agglutinating red blood cells in the sample in the absence of endotoxin, and wherein, following addition of construct to the sample, the presence of the analyte in the sample leads to a decrease in the time required for agglutination or in the extent of agglutination at a selected time as compared to an appropriately-selected control.

40. The composition of claim 39 wherein the lectin is phytohemagglutinin.

\* \* \* \* \*